US005725153A

United States Patent [19]

Wang et al.

[11] Patent Number: 5,725,153

[45] Date of Patent: Mar. 10, 1998

[54] OSCILLATING CAPILLARY NEBULIZER

[75] Inventors: Lanqing Wang; Richard F. Browner, both of Atlanta, Ga.

[73] Assignee: Georgia Tech Research Corporation, Atlanta, Ga.

[21] Appl. No.: 370,734

[22] Filed: Jan. 10, 1995

[51] Int. Cl.$^6$ .......................... A61M 16/00; A61M 11/02

[52] U.S. Cl. ........................ 239/102.1; 239/420; 239/424

[58] Field of Search .............................. 239/402.1, 434.5, 239/420, 423, 424

[56] References Cited

U.S. PATENT DOCUMENTS

| | | | |
|---|---|---|---|
| Re. 25,744 | 3/1965 | Drayer . | |
| Re. 33,642 | 7/1991 | Lester . | |
| 2,532,851 | 12/1950 | Meyer | 239/420 |
| 2,887,181 | 5/1959 | Dillon . | |
| 2,966,312 | 12/1960 | Wilson, Jr. et al. . | |
| 3,108,749 | 10/1963 | Drayer . | |
| 3,292,868 | 12/1966 | McCartney et al. | 239/424 |
| 3,421,699 | 1/1969 | Babington et al. . | |
| 3,790,079 | 2/1974 | Berglund et al. . | |
| 4,112,297 | 9/1978 | Miyagi et al. . | |
| 4,161,281 | 7/1979 | Erb et al. . | |
| 4,209,696 | 6/1980 | Fite . | |
| 4,268,460 | 5/1981 | Boiarski et al. . | |
| 4,298,795 | 11/1981 | Takeuchi et al. . | |
| 4,300,044 | 11/1981 | Iribarne et al. . | |
| 4,403,147 | 9/1983 | Melera et al. . | |
| 4,629,478 | 12/1986 | Browner et al. . | |
| 4,638,945 | 1/1987 | Toda et al. . | |
| 4,687,929 | 8/1987 | Browner et al. . | |
| 4,728,036 | 3/1988 | Bennett et al. | 239/420 |
| 4,762,995 | 8/1988 | Browner et al. . | |
| 4,924,097 | 5/1990 | Browner et al. . | |
| 4,960,244 | 10/1990 | Maag et al. | 239/424 |

FOREIGN PATENT DOCUMENTS

| | | | |
|---|---|---|---|
| 56-1-2959 | 8/1981 | Japan . | |
| 58-40165 | 3/1983 | Japan . | |
| 35-11621 | 4/1986 | Japan . | |
| 5138080 | 6/1993 | Japan | 239/102.1 |
| 2 203 241 | 10/1988 | United Kingdom . | |

OTHER PUBLICATIONS

Direct Injection Nebulization for Inductivity Coupled Plasma Mass Spectrometry—Wiedrin et al., Anal. Chem. 1991, 63, 219–225.

Spatially Resolved Measurements of Size and Velocity Distributions of Aerosol Droplets from a Direct Injection Nebulizer—Shum et al., Appl. Spectros., vol. 47, No. 5, 1993.

Brochure for Meinhard TR 30–C3 Nebulizer; ICP Information Newelstter, vol. 19, No. 6, 408 (Nov. 1993).

Weiderin and Houk, Measurements of Aerosol Particle Sizes from a Direct Injection Nebulizer; Appi. Spectrosc., 45, 1408 (1991).

Olesik et al., Inductivity Coupled Plasma Optical Emission Spectrometry Using Nebulizers With Widely Different Sample Consumption Rates; Anal. Chem., 66, 2022, (1994).

Weiner, B.B., Particle and Droplet Sizing Using Fraunhoffer Diffraction.

*Primary Examiner*—Matthew C. Graham
*Attorney, Agent, or Firm*—Deveau, Colton & Marquis

[57] ABSTRACT

An oscillating capillary nebulizer which is capable of nebulizing a liquid sample flow at micro flow liquid flow rates and which is capable of controlling the particle size and particle size distribution of the nebula. The oscillating capillary nebulizer comprises a pair of coaxial capillary tubes which are friction-fit mounted by way of peek tubing ferrules. The dimensions of the inner and outer capillary tubes are such that an annular spacing is created between the inner surface of the outer capillary tube and the outer surface of inner capillary tube. A liquid sample is introduced into the nebulizer through the inner capillary tube. A gas flow path is provided by the space between the inner and outer capillary tubes. The gas enters the gas flow path through a port in the side of the outer capillary tube. At least the inner capillary tube is made of flexible material. Preferably, the inner diameter of the inner capillary tube is small enough to provide jet flow of the liquid sample at low liquid flow rates. The gas flow velocity, which is a function of the gas flow rate and the size of the annular spacing, is sufficient to cause turbulence of the gas stream around the free end of the inner capillary tube, thereby creating instability in the system. This instability, depending on how the system is set up, will initially cause the inner capillary tube to oscillate. The oscillation causes the generation of a high frequency standing wave along a portion of the length of the inner capillary and a breakup of the liquid jet into uniform liquid drop sizes.

8 Claims, 8 Drawing Sheets

OSCILLATING CAPILLARY NEBULIZER

BACKGROUND OF THE INVENTION

The present invention relates to a method and apparatus for generating a aerosol and, more particularly, a oscillating capillary nebulizer which is capable of nebulizing a liquid flow at microflow liquid flow rates ad controlling the particle size and the particle size distribution of the nebulized particles.

Typical pneumatic nebulizers, such as the Meinhard TR 30-C3 nebulizer, operate at liquid sample flow rates of about 500 μl/min or greater. The Meinhard nebulizer consists of a rigid inner glass capillary tube drawn to a fine tip, surrounded by another glass tube dram concentrically to a conical tip. The nebulizer operates through the interaction of a liquid stream in the inner capillary and a gas stream in the annular space between the capillary tubes causing droplet formation. The Meinhard nebulizer suffers from a number of drawbacks, including that it tends to block up due to its converging tip. Once blocked, it is usually discarded.

Nebulizers which employ parallel coaxial tubes tend to avoid blockage problems. One such nebulizer is that of the application GB 2 203 241 to Willoughby et al. In this nebulizer velocity of the entraining gas combined with thermally induced solvent evaporation serves to cause a breakup of the liquid sample jet into liquid particles to produce an aerosol. This nebulizer is described to operate over liquid sample flow rates from 10–2000 μl/min. However, such nebulizers are not known to work well at low liquid flow rates or when the end of the inner capillary tube extends out beyond the end of the outer capillary tube. By low liquid flow rates, we mean 500 μl/min or less. This nebulizer is not described to cause an oscillation of the capillary tube by creating instability in the system, but rather describes that the aerosol is created by the combination of the entraining gas velocity and liquid sample heating. Another example of a known nebulizer which incorporates a coaxial tube arrangement is disclosed in U.S. Pat. No. 4,924,097 to Browner et al.

Another form of such a nebulizer is the direct injection nebulizer (DIN) of Wiederin et al. for inductively coupled plasma mass spectrometry (ICP/MS). Anal. Chem., 63, 219–225 (1991). Wiederin et al. disclose a DIN assembly consisting of a length of fused silica capillary tubing having a 50 μm inner diameter and a 200 μm outer diameter disposed within a stainless steel tube serving as the nebulizer. The stainless steel tube has a 250 μm inner diameter and a 1.6 μm outer diameter. Thus, a 25 μm annular space is provided between the stainless steel tube and the fused silica capillary tubing. The inner tubing is positioned to extend approximately 100 μm beyond the end of the stainless steel nebulizer tube. The DIN assembly is positioned within the converging end of the quartz injector tube of the torch for injecting sample directly into the plasma of the ICP/MS. As shown by FIG. 3, the liquid sample flow rate was optimized at 120 μl/min. with a corresponding gas nebulizer gas pressure of 200 psi and a nebulizer gas flow rate of 1.0 L/min. In operation, Wiederin et al. observed a slight hissing sound, like most pneumatic nebulizers, which became quite loud when the plasma was started and liquids were ,nebulized. Wiederin et al, comment that the precision of their nebulizer was notably poorer when positioned in a spray chamber similar to a conventional pneumatic nebulizer.

The operation of the Wiederin et al. DIN assembly has been categorized by Shum et al. See Appl. Spectrosc. 47, 575, (1993). When the Wiederin et al. DIN assembly was operated at a liquid flow rate of 100 μL/min., it was found that the inclusion of methanol as an organic modifier to a liquid water sample had a dramatic effect on the size of the aerosol droplet distribution attained, as illustrated by Shum et al. in FIG. 2. It was also observed that varying nebulizer gas flow rates from 0.3–0.9 L/min., while maintaining the liquid sample flow rate constant, had little effect on the size of aerosol droplets obtained.

It is also known in the prior art to utilize ultrasonic transducers to break up a liquid sample jet into liquid droplets. For example, Miyagi et al., U.S. Pat. No. 4,112,297, disclose a nebulizer which includes an ultrasonic transducer used to create the particle beam. Melera et al,, U.S. Pat. No. 4,403,147, incorporate an acoustic transducer, such as a piezoelectric transducer which may be used to stimulate the probe to break up the liquid stream. An example of a nebulizer which employs an oscillating piezoelectric ceramic transducer is disclosed in Berglund, U.S. Pat. No. 3,790,079. In such nebulizers, which operate on the basis of a transducer, the frequency of operation effects the aerosol droplet size. They also are much more expensive than a co-axial tube nebulizer.

It is also known in the prior art to utilize an electrospray technique which incorporates a fine capillary tube made of conducting metal attached to a high voltage source. An example of this technique is disclosed in Fite, U.S. Pat. No. 4,209,696.

Drayer et al., U.S. Pat. No. 3,108,749, and a Reissue patent to Drayer et al., RE.25,744, are representative of other forms of pressurized air induced vibrating atomizers.

None of the above described nebulizers or atomizers are known to operate reliably at micro flow liquid flow rates. By micro flow liquid flow rates, we mean 50 μl/min or less and preferably below 30 μl/min. Conventional nebulizers typically operate at liquid flow rates greater than 500 μl/min. However, at such liquid flow rates the solvent delivery rate to any mass spectrometer or plasma source detector will be so great as to cause considerable source instability. Hence, a solvent removal step, through either a droplet removal chamber or a two-(or three-)stage pressure reduction skimmer device is necessary. With benchtop LC/MS systems, the relatively low pumping capacity of the source makes coupling with high flow nebulizers impractical. At liquid flow rates of about 500 μl/min or less, the conventional nebulizer becomes unsatisfactory and unreliable. The lowest liquid flow rate reported by Wiederin et al. for their direct injection nebulizer is 30 μl/min. However, they teach away from such lower flows by teaching that the liquid flow rate was optimized at 120 μl/min.

Therefore, a need exists in the art for a nebulizer which is capable of producing an aerosol at microflow liquid flow rates for employment with microflow chromatographic techniques and for use with bench top LC/MS, ICP/AES and ICP/MS instruments and which is capable of satisfactorily controlling the particle size and particle size distribution of the aerosol. Accordingly, the present invention employs an inner/outer coaxial tube arrangement which can accomplish this goal without utilizing the electrospray technique or without utilizing a transducer to stimulate the tube in order to create an aerosol at micro flow liquid flow rates.

SUMMARY OF THE INVENTION

Accordingly, the present invention utilizes a novel inner/outer coaxial tube arrangement which is capable of creating an aerosol at microflow liquid flow rates particularly for use with chromatographic techniques and for use with bench top LC/MS, ICPAES and ICP/MS instruments, among others, and which is capable of controlling the particle size and particle size distribution of the aerosol. The present invention comprises a pair of coaxial capillary tubes which are disposed in parallel to one another and which are preferably friction-fit mounted by way of PEEK tubing ferrules. The dimensions of the inner and outer capillary tubes are such that an annular spacing is created between the outer surface of the inner capillary tube and the inner surface of the outer capillary tube. A rotating connector ring or fitting may be included to allow the position of the inner capillary tube to be adjusted in the coaxial directions relative to the outer capillary tube.

A liquid sample is introduced into the nebulizer through the inner capillary tube. A gas flow path is provided by the annular space between the inner and outer capillary tubes. The gas enters the gas flow path through an opening in the side of the outer capillary tube. At least the inner capillary tube is made of a flexible material, preferably polyamide coated fused silica. The outer capillary tube may be made of either a flexible material or an inflexible material. Preferably, the inner diameter of the inner capillary tube is small enough to provide jet flow of the liquid sample at microflow liquid flow rates. The gas flow velocity, which is a function of both the gas flow rate and the size of the annular space, is sufficient to cause turbulence of the gas stream around the end of the inner capillary tube, thereby creating instability in the system. This instability, depending on how the system is set up, will first cause initially the inner capillary tube to oscillate and possibly also the outer capillary tube, if the outer capillary tube is also made of a flexible material. The position of the inner tube relative to the outer tube is not critical, and the inner tube may be extended or retracted up to about 1.25 mm from the end of the outer tube. However, optimum performance is obtained either with the two tubes approximately flush with one another, or the inner tube extending slightly beyond the end of the outer tube, depending on the gas flow rates. The oscillation causes the generation of a high frequency standing wave along a portion of the length of the inner capillary tube which then transmits the energy to the liquid stream causing the breakup of the liquid sample stream exiting the inner capillary tube into small liquid drop sizes.

The present invention produces aerosol particles at lower liquid flow rates than is known possible with the prior art devices. The typical prior art nebulizers generally operate at liquid flow rates of approximately 50 μl/min. to 1–2 ml/min. These types of nebulizers rely on the direct interaction between gas velocity and liquid jet to cause a breakup of the liquid jet into liquid particles. By operating at a lower liquid flow rate than the prior art nebulizers, the nebulizer of the present invention is able to achieve greater control over particle size and particle size distribution, more uniform particle sizes and smaller mean particle sizes than before. Furthermore, the particle drop sizes found are not much influenced by the surface tension or viscosity of the solvents used with typical pneumatic nebulizers.

In the preferred embodiment, the capillary tubes are replaceable in case of either breakage or blockage.

Accordingly, it is an object of the present invention to provide an oscillating capillary nebulizer which is capable of generating aerosol at lower liquid flow rates than is capable with the prior art nebulizers.

It is another object of the present invention to provide an oscillating capillary nebulizer which is capable of producing a primary aerosol distribution having smaller mean droplet sizes than prior known pneumatic nebulizers.

It is another object of the present invention to provide an oscillating capillary nebulizer which is capable of being used with bench top liquid chromatograph and mass spectrometer instrument systems and microflow separation techniques such as LC and CE combined with ICP/AES, ICP/MS, FT-IR, FT-MS and MS/MS.

It is another object of the present invention to provide an oscillating capillary nebulizer which is capable of achieving better control over the particle size and particle size distribution of aerosol droplets generated.

It is another object of the present invention to provide an oscillating capillary nebulizer which is capable of achieving results similar to those achieved by ultrasonic nebulizers at greatly reduced costs and without the need for employing a transducer or electrospray techniques to break up the liquid stream.

It is another object of the present invention to provide an oscillating capillary nebulizer which is capable of operating over a wide range of liquid and gas flow rates.

It is another object of the present invention to provide an oscillating capillary nebulizer which is less sensitive to the gas employed and the gas flow rate than conventional nebulizers.

It is yet another object of the present invention to provide an oscillating capillary nebulizer which is effective at both atmospheric and reduced pressure.

These and other objects of the present invention will be apparent from the detailed description of the invention.

DETAILED DESCRIPTION OF THE INVENTION

Figure 1:
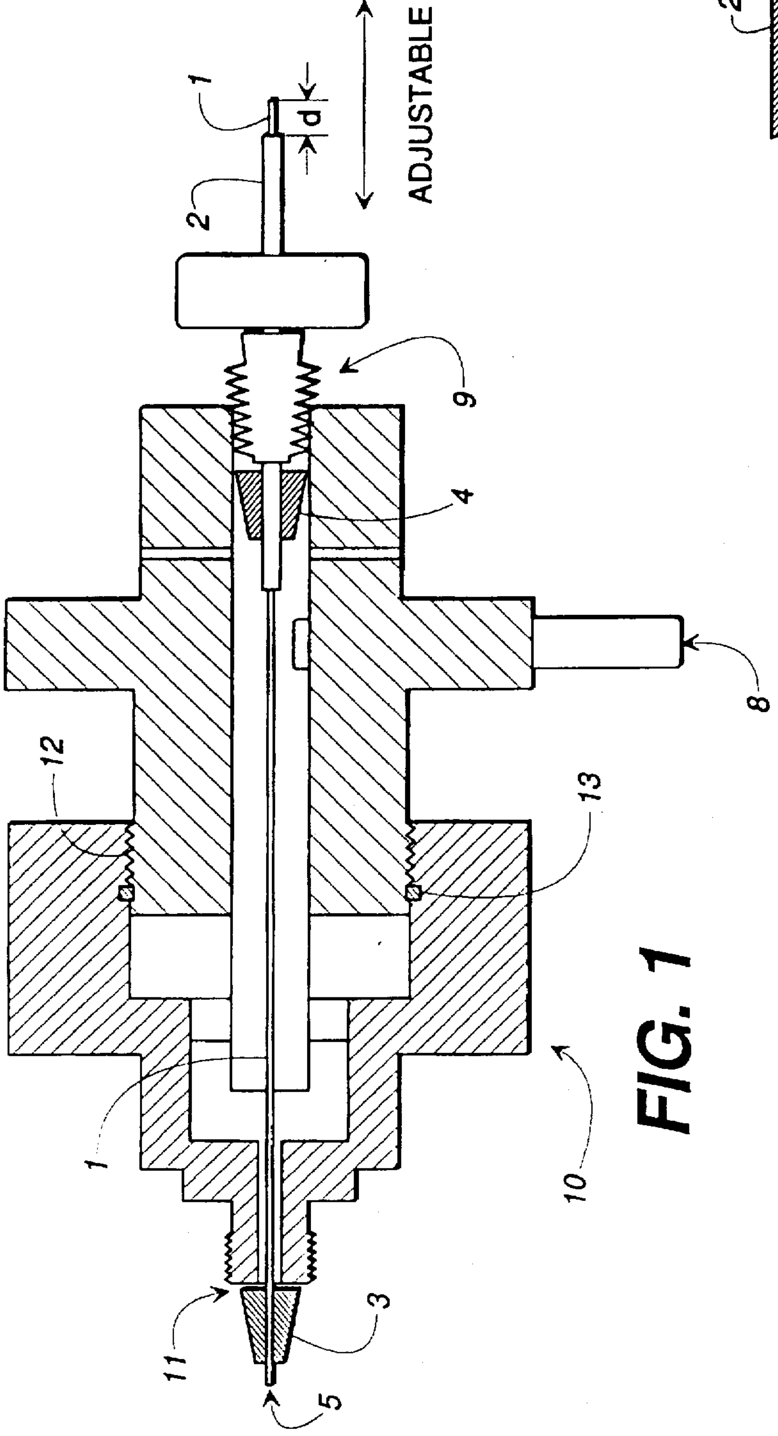
FIG. 1 illustrates a cross-sectional side view of the oscillating capillary nebulizer of the present invention.
Figure 2:
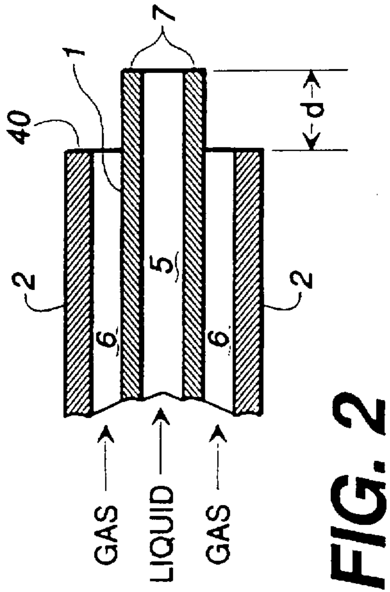
FIG. 2 illustrates a cross-sectional view of the coaxial arrangement of the inner and outer capillary tubes of the present invention.
Figure 3:
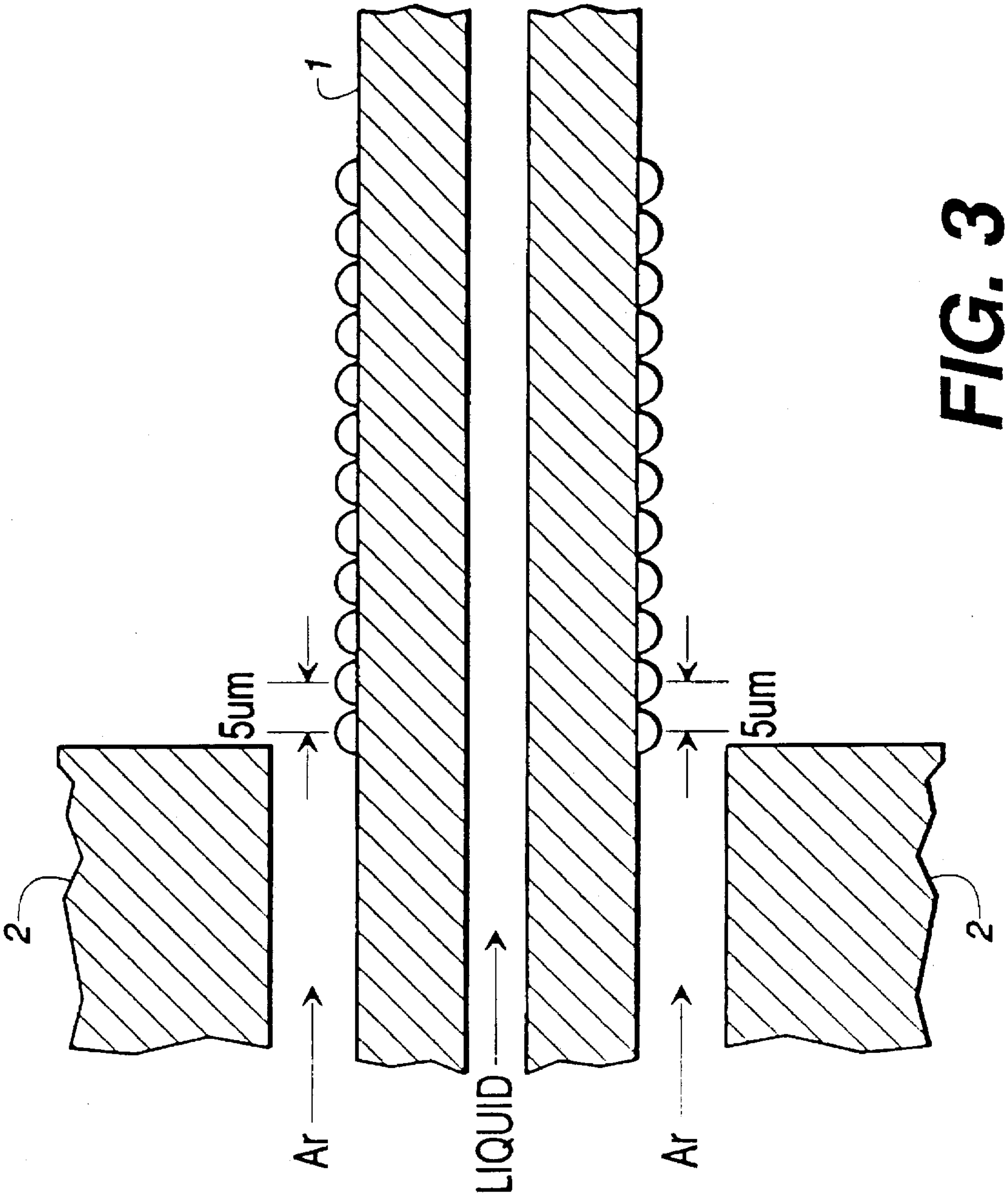
FIG. 3 illustrates a trace of the ultrasonic wave observed on the inner capillary tip of the oscillating capillary nebulizer of the present invention.

As shown in FIGS. 1 and 2, the oscillating capillary nebulizer of the present invention is comprised of a pair of coaxial inner and outer capillary tubes 1, 2. The capillary tubes are friction-fit mounted by way of PEEK tubing ferrules 3 and 4 near their proximal ends 10 and 12, respectively. This fitting allows for interchangeability and replacement of capillary tubes. Liquid sample introduction, generally from a liquid chromatography, is provided by liquid flow path 5 via the inner capillary tube 1. A gas flow path is provided by the annular space 6 between the outer diameter of the inner capillary tube 1 and the inner diameter of the outer capillary tube 2. The gas enters the gas flow path through an port 8 in the side of the outer capillary tube. At least the inner capillary tube 1 is made of a flexible material, preferably polyamide coated fused silica (Polymicro Technology, Inc., which adds flexibility and makes the tubing less brittle).

The outer capillary tube 2 may also, but need not, be made of a flexible material. The dimensions of the inner capillary tube 1 are such that a flow of the liquid sample is provided at flow rates as low as 50 μl/min. and less.

A connector 11 is shown for allowing connection of the liquid sample input of the nebulizer to a ZDV union. The nebulizer is further constructed with a rotating connector ring 12 sealed by O-ring 13.

With reference to FIG. 2, the inner and outer capillary tubes are arranged to provide relative movement between them in the axial directions. Preferably, a rotating connector ring or fitting 9 allows the outer capillary tube to be moved in the axial direction such that the distance that the distal end 40 of the outer capillary tube 2 extends in relation to end 7 of the inner capillary tube 1 can be adjusted.

Figure 4:
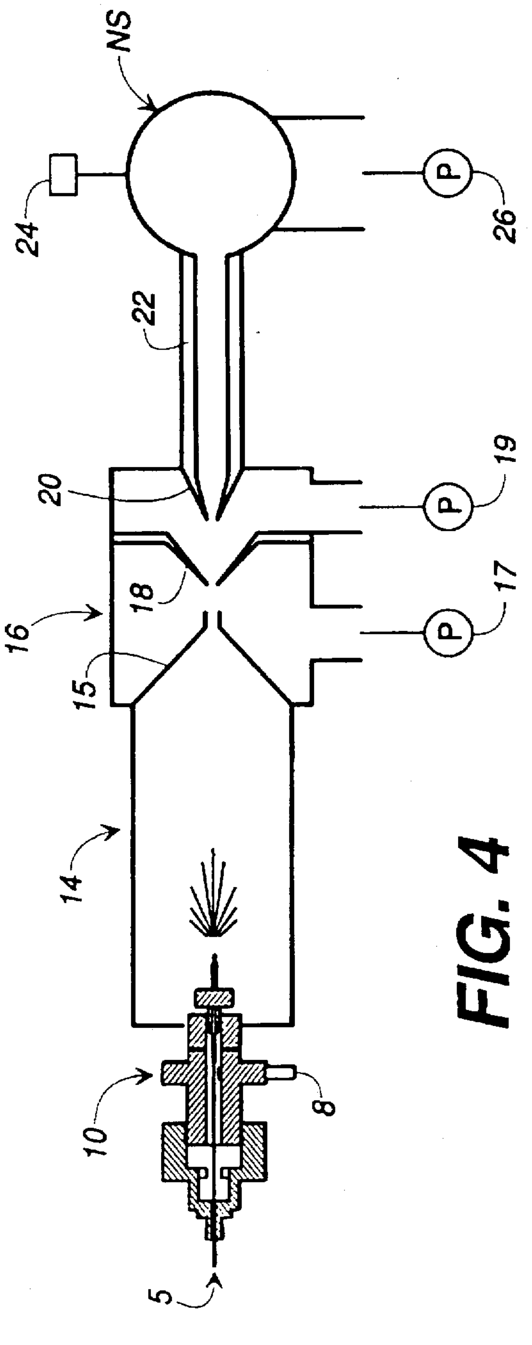
FIG. 4 illustrates the oscillating capillary nebulizer of the present invention combined with a PB LC/MS system.

In operation, the gas flow velocity must contain sufficient kinetic energy to cause turbulence of the gas stream around the distal end 7 of the inner capillary tube and impart instability in the system. This gas flow velocity is a function of the gas flow rate and the size of the annular space 6 between the capillary tubes. In order to create this instability, sufficient gas velocity for a particular gas is needed to cause the inner capillary tube to oscillate and generate an ultrasonic standing wave along the axial direction of at least a portion of the inner capillary tube, as illustrated in FIG. 4. This instability will also cause the inner capillary tube to transversely oscillate at a low frequency, and depending on how the system is set up, may also cause the outer capillary tube to oscillate if also made of a flexible material. The oscillation of the inner capillary tube is observable in both the transverse and longitudinal directions. The oscillation in the transverse direction is typically in the range of 200 Hz to 1400 Hz and is audible. However, it is the longitudinal oscillation that appears to generate the standing wave. The oscillation is in the megahertz to tens of megahertz range and is inaudible. In one set of conditions we observed the wavelength of the longitudinal oscillation was about 5 μm. The longitudinal oscillation of the inner capillary tube causes a breakup of the liquid jet into uniform liquid drop sizes. The oscillating capillary nebulizer of the present invention is capable of operating to produce aerosol over a liquid micro flow rate range of 50 μl/min or less. The gas flow rate range is generally from 0.5 liters/min. to 1.0 liters/min. The instability of the inner capillary tube or inner and outer capillary tubes is a function of the location of the distal end 7 of the inner capillary tube 1 with respect to the distal end 8 of outer capillary tube 2, the dimensions of the inner and outer capillary tubes 1 and 2, and the gas and liquid flow rates.

FIG. 4 illustrates the oscillating capillary nebulizer 10 of the present invention interfaced with a mass spectrometer MS sometimes referred to as a PB LC/MS. The interface is a conventional interface of the type shown in U.S. Pat. Nos. 4,687,929, 4,762,955, 4,629,478 and 4,924,097 to Browner et al. The interface consists of a desolvation chamber 14 into which the aerosol generated by the oscillating capillary nebulizer is introduced. The aerosol proceeds through the conical end 15 of the desolvation chamber into the momentum separator 16. The momentum separator may consist of one or two chambers, two chambers being shown separated by cone skimmer 18. As illustrated, a second cone skimmer 20 leads to outlet tube 22 and onto the mass spectrometer MS. The mass spectrometer is a conventional mass spectrometer including an ion source 24 and a diffusion pump 26. Vacuum pumps 17 and 19 serve to draw vacuum in the momentum separator portion of the interface providing for the low pressure interface to the mass spectrometer.

Figure 5:
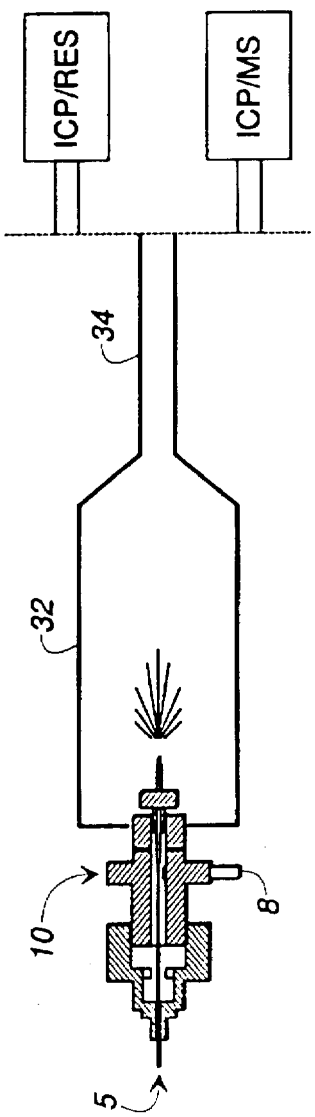
FIG. 5 illustrates the oscillating capillary nebulizer of the present invention and an interface for either an ICP/AES or an ICP/MS system.

In FIG. 5, the oscillating capillary nebulizer 10 of the present invention is shown with an interface for either an ICP/AES or ICP/MS system for operation at atmospheric pressure. In this application, the aerosol of the oscillating capillary nebulizer is introduced into a spray chamber 32 which is coupled with transfer tubing 34 leading to either the ICP/AES or the ICP/MS system. The OCN can also be used as an interface between micro LC to ICP-AES or ICP-MS.

EXPERIMENTAL

The oscillating capillary nebulizer of the present invention was constructed as described above with, reference to FIG. 1 with lengths of the liquid and gas capillary tubes 1, 2 being 80±10 mm. and 30±10 min., respectively. The rotating connector fitting 9 was used, when necessary, to adjust the position of the outer capillary tube 2 relative to the one in the axial direction relative to the position of the inner capillary tube 1. The adjustable distance between the tips of both capillaries was in the range of −2 min. to +3 mm.; the negative values indicating that the inner capillary tube was retracted inside the gas capillary tube, and the positive values indicating that the distal end of the liquid capillary tube was extending beyond the distal end of the gas capillary tube. The capillary tubes were friction-fit mounted by PEEK tubing ferrules allowing for easy change of either or both capillary tubes. In this way, the four diameters of the capillary tubes, namely, the inner and outer diameters of each tube could be manipulated, simply by swapping out the capillary tubes.

The liquid samples were introduced into the liquid capillary tube 1 by a Hewlett-Packard Model 1090 Liquid Chromatography Pump which is capable of delivering continuous liquid flows with 1 μl/min. resolution. At liquid flow rates of 10 μl/min. or less to cancel pulsation of the pump, a short length of 20 μm i.d. silica capillary tube was placed in line between the pump and the liquid capillary 1. A Matheson mass flow controller Model 8270 was used to control the nebulizer gas flow rate. The back pressure for the gas flow rate was 120 psi for the oscillating capillary nebulizer of the present invention, unless otherwise specified.

A Malvern (Southborough, Mass.) 2600c Droplet and Particle Sizer was used for measuring aerosol drop size distributions. This instrument consists of a helium/neon laser beam, a receiver lens, and a series of 31 semi-circular concentric annular detectors in addition to a central detector. The operating principle of the Malvern system is based on the Fraunhoffer diffraction theory. B. B. Wiener, "Particle and Droplet Sizing Using Fraunhoffer Diffraction," in Modern Methods of Particle Size Analysis, H. G. Barth, ed. John Wylie & Sons, N.Y. (1984). By measuring the scattering of the small forward angle, histogram plots of volume percent versus particle size of aerosol can be provided. Unfortunately, the measurable particle range is limited to 1.9 μm to 176 μm by this theory. Especially for 1–2 μm particles, the errors can be 20% or more. In spite of these limitations, laser Fraunhoffer scattering systems have been used extensively for measuring aerosol from atomic spectrometric systems and have inherent advantages. See also, D. R. Wiederin and R. S. Houk, Appl. Spectrosc., 45, 1408, (1991); and J. W. Olesik, J. A. Kinzer and B. Harkelroad, Anal. Chem., 66, 2022, (1994). It is non-intrusive, precise, absolute, and fast.

The Fraunhoffer particle sizer provides a great deal of information about aerosol size distribution. To relate the aerosol properties to the analytical atomic spectrometric signals, two important parameters are used: the Sauter Mean Diameter ($D_{3,2}$) and the drop size distribution. The Sauter mean diameter is a measure of a total volume of particles in a distribution compared to the surface area. Mathematically, it can be expressed as the following formula:

$$D_{3,2}=\{\Sigma d_j^3 N_j/\Sigma d_j^2 N_j\}$$

where $d_a$ is the jth diameter and $N_j$ is the number of particles of diameter $D_j$.

For a given analyte concentration the analyte mass contained in the aerosol is directly proportional to aerosol volume. Moreover, the evaporation and vaporization rates of particles are inversely related to the volume-to-surface area ratios. The lower the $D_{3,2}$, the faster evaporation and vaporization occur, resulting in a higher signal. The drop size distribution obtained by the Fraunhoffer scattering is percent volume distribution which can be readily transposed into a mass distribution and knowing the solvent and analyte density.

In our experiments, a lens of 63 mm focal length was used and particle size range observed was 1.22 to 118 μm. The Malvern instrument was operated using the "independent mode" option. The primary aerosols were perpendicularly introduced into the helium/neon laser beam directly from the nebulizer at a distance of 14 mm for all measurements. Each measurement was made in triplicate and all data were an average of the three measurements. The information provided by the particle sizer is percent volume based on drop-size distribution. Argon was used as the nebulizer gas for all nebulizers. Distilled de-ionized water, and methanol were used as solvents.

Figure 6:
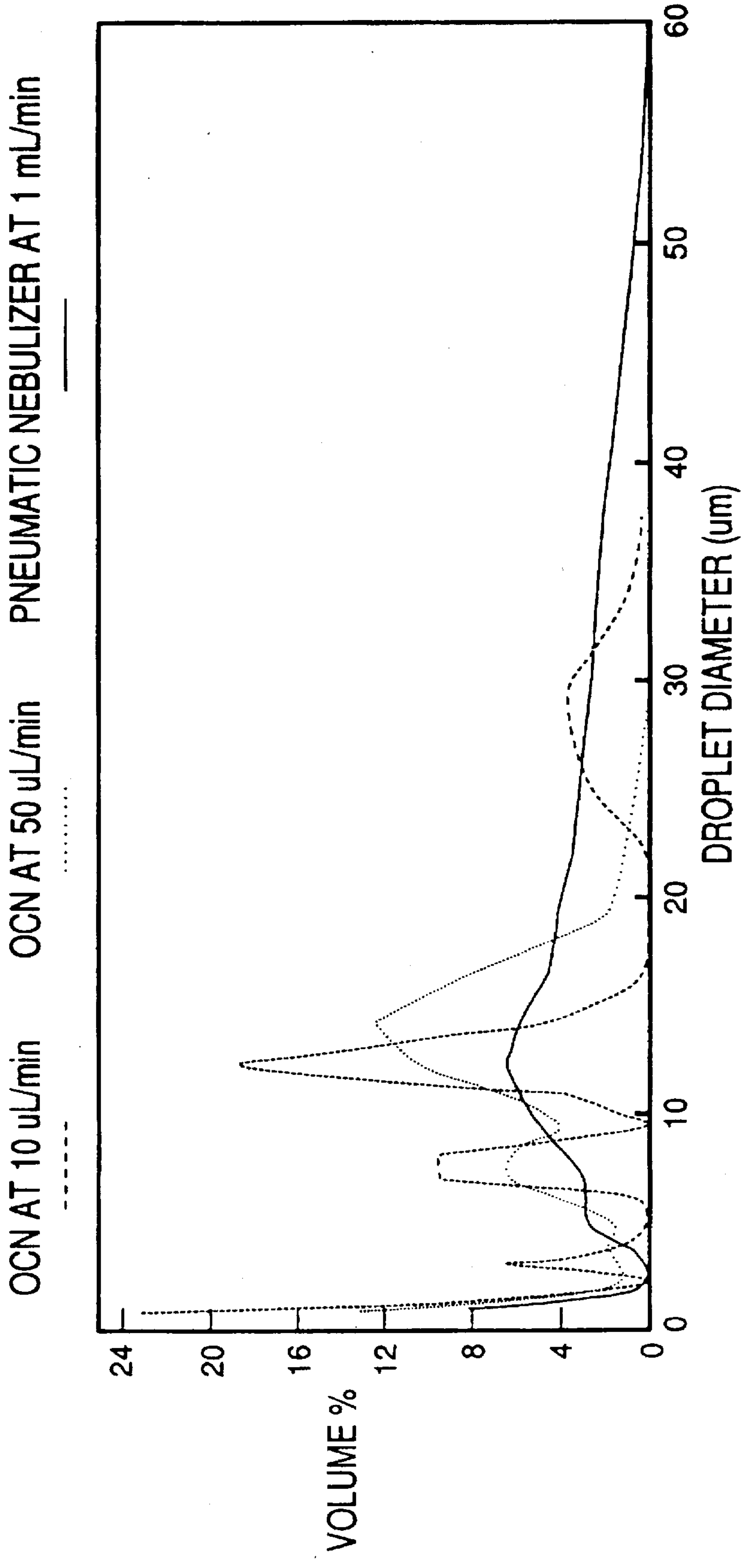
FIG. 6 illustrates the primary aerosol distributions for the oscillating capillary nebulizer of the present invention and a conventional nebulizer at an argon carrier gas flow rate of 0.90 L/min.

Using the above-described experimental arrangement, the effect of liquid sample uptake rates on the primary aerosol distributions of the oscillating capillary nebulizer of the present invention was studied with results for liquid flow rates of 50 and 10 μl/min. illustrated in FIG. 6. For this study, the liquid capillary tube used had an inner diameter of 50 μm and an outer diameter of 142 μm. The gas capillary tube had an inner diameter of 250 μm and an outer diameter of 440 μm. 100% water was used as the liquid sample stream, and argon at a flow rate of 0.90 l/min. was used as the gas carrier. The results demonstrate that not only was the oscillating capillary nebulizer of the present invention capable of operating at microflow liquid sample flow rates, but that at the lower liquid flow rates the aerosol particle size distribution becomes more sharply defined. Though better results are obtained at the lower micro flow liquid flow rates, additional studies showed that the nebulizer of the present invention is also operable at higher flow rates of upwards of 1–2 ml/min.

One of the distinguishing characteristics of the OCN operated at micro flow rates is the production of aerosols with multimodal size distributions. These typically show 3–4 peaks which appear to correspond to a harmonic series, such as 4 μm, 8 μm and 12 μm. The numbers and portions of the peaks vary somewhat with nebulizer operating conditions. The peaks are considered to correspond to multiple frequencies present in the longitudinal standing wave on the inner capillary.

Also shown in FIG. 6 is the primary aerosol distribution for the Meinhard nebulizer Model 12 30-C3 operated at a liquid flow rate of 1 mL/min, a typical liquid flow rate for this nebulizer and at an argon gas flow rate of 0.90 L/min. The aerosol distribution achieved for this nebulizer is considerably flatter and more disperse than the primary aerosol distributions achieved by our nebulizer.

Figure 7:
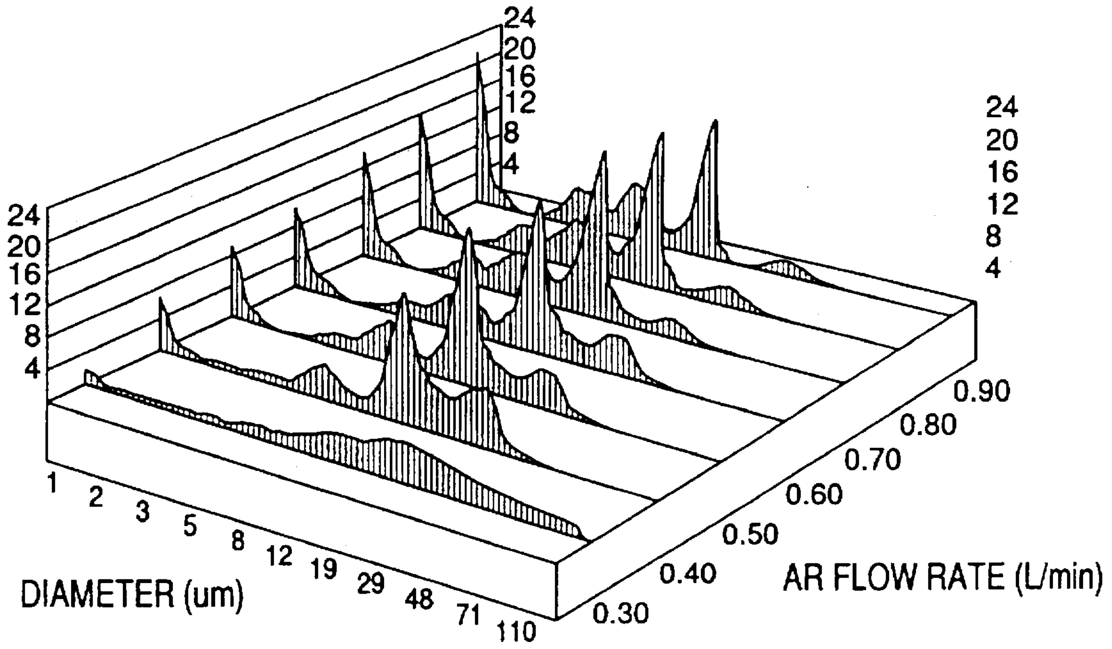
FIG. 7 illustrates the effect of argon nebulizer flow rate on the primary aerosol distributions of the oscillating capillary nebulizer of the present invention.

The effect of the gas flow rate on the primary aerosol distribution of the present invention was also studied, which results are illustrated in FIG. 7. In this study, the liquid and gas capillary tubes were of the same inner and outer diameters as employed with regard to the study of the sample uptake rate (FIG. 6). 100% water was used at a liquid flow rate of 50 μl/min. The gas used was argon. We see that increasing the gas flow rate increased the performance of our nebulizer. For this particular arrangement, having an annular spacing of approximately 54 microns, a gas flow rate of greater than 0.30 L/min. was necessary to provide sufficient gas velocity to the annular spacing to impart the desired instability and oscillation of the inner capillary tube.

We have found that our nebulizer works, not only with argon, but with a wide range of carrier gases including air, helium, nitrogen, oxygen. This in contrast to the conventional pneumatic nebulizer, such as the Meinhard nebulizer, which does not work well with, for example, helium as the carrier gas. Thus, we have found that our present nebulizer is less sensitive to the type of carrier gas employed than conventional nebulizers.

Figure 8:
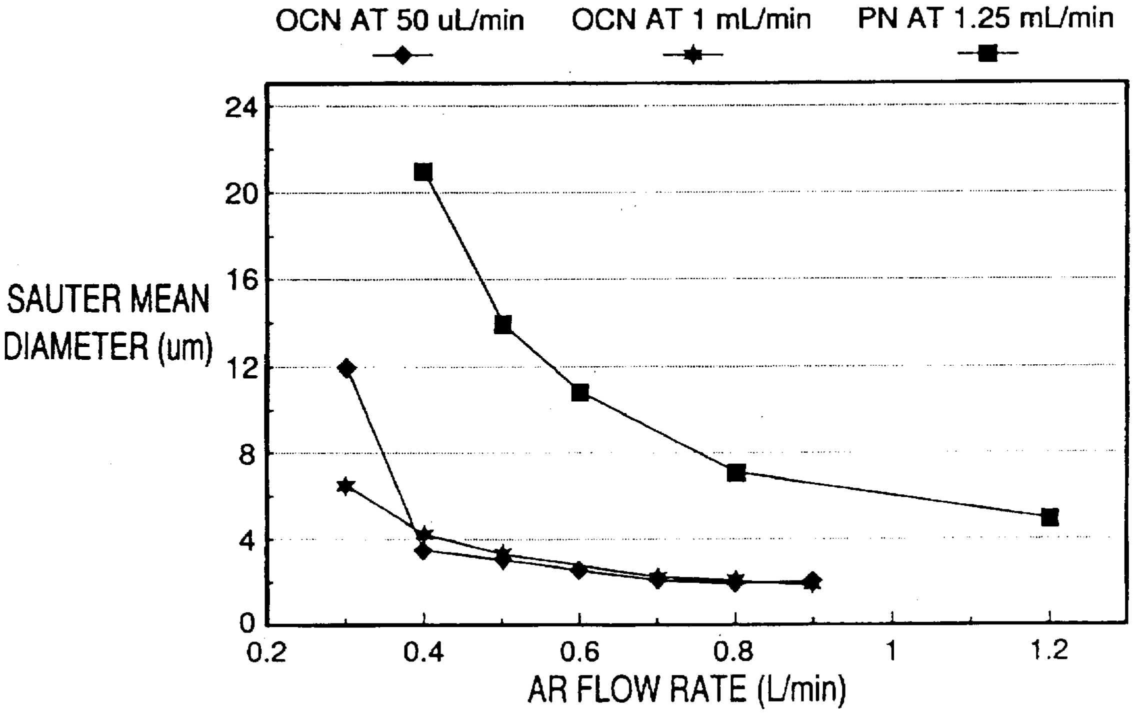
FIG. 8 illustrates the variation of Sauter mean droplet diameter with gas flow for methanol liquid solvent and argon nebulizing gas for both the oscillating capillary nebulizer of the present invention and a conventional nebulizer.

FIG. 8 illustrates the variation of Sauter mean droplet diameter with gas flow for both the present invention and the Meinhard TR 30-C3 nebulizer. In all three runs the liquid solvent was methanol and the nebulizing gas was argon. In contrast to the results obtained from the Meinhard nebulizer, our nebulizer experienced a significant reduction in mean droplet diameter for increasing nebulizing gas flow from 0.3 to 0.4 L/min. Furthermore, our nebulizer enjoyed significantly lower mean particle diameters than those achieved by use of the Meinhard nebulizer.

Figure 9:
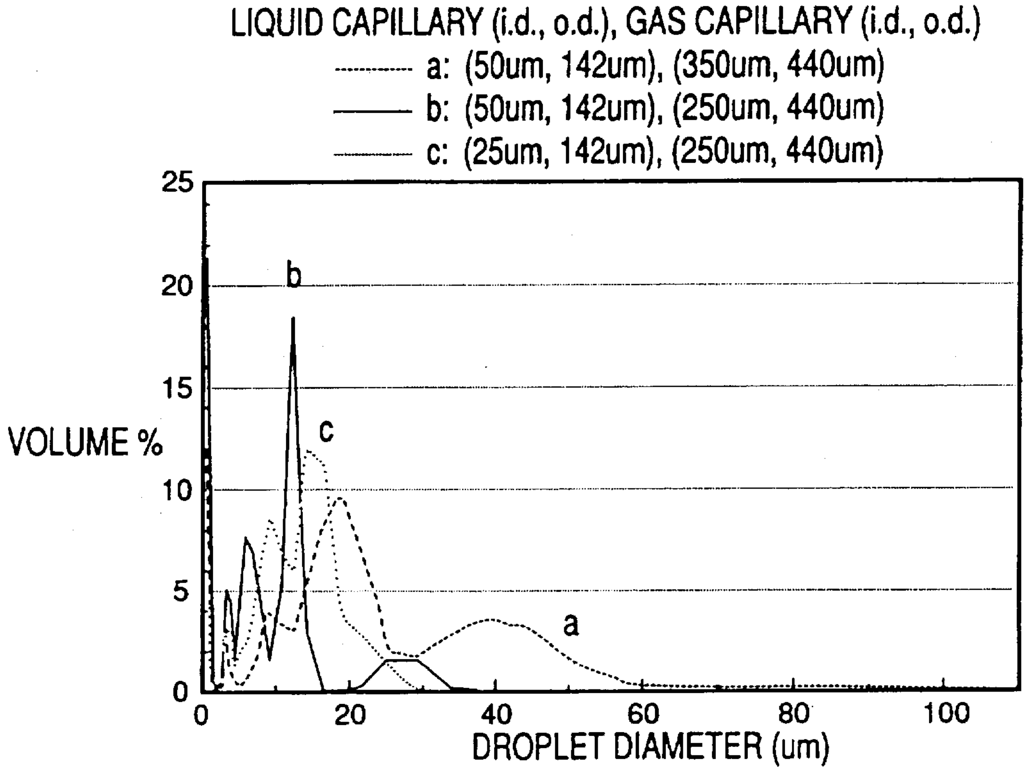
FIG. 9 illustrates the effect of capillary dimensions on the primary aerosol distribution of the oscillating capillary nebulizer of the present invention.

FIG. 9 illustrates the effect of the dimensions of the inner and outer capillary tubes on the primary aerosol distribution of our nebulizer. In this study, 100% water was used at a flow rate of 50 μl/min. Argon was used as the carrier gas at a flow rate of 0.90 L/min. Curve a reflects the results using our nebulizer with the liquid capillary tube having an inner diameter of 50 μm and an outer diameter of 142 μm, and a gas capillary tube having an inner diameter of 350 μm and an outer diameter of 440 μm. Curve b reflects the results using the same size inner liquid capillary, but a smaller gas capillary tube having an inner diameter of 250 μm and an outer diameter of 440 μm. A noticeable difference between the primary aerosol distributions of curves a and b is seen, which is believed to be due to the difference in the size of the annular space between the inner and outer capillaries. Curve b represents an annular spacing of approximately 54 μm while curve a represents an annular spacing of approximately 104 μm, resulting in a significant shift of the aerosol size distribution to larger droplet diameters with the larger annular spacing. This difference is believed to be due to the resulting lower gas flow velocity through the larger annular spacing represented by curve a.

On the other hand, curve c represents the results using our nebulizer having the same outer gas capillary tube as in curve b, but the inner liquid capillary tube having an inner diameter of 25 μm and an outer diameter of 142 μm, representing the smaller annular spacing at 45 μm and also a smaller passageway for the liquid sample. This change to a smaller inner diameter of the liquid capillary tube demonstrated little difference in the performance of our nebulizer. The slight change to a larger aerosol droplet distribution is believed to be due to the thicker wall of the inner capillary tube used in Test C which would cause a stiffer, and therefore less flexible, inner tube.

With reference to FIGS. 8 and 9, it can be seen that the gas velocity for a particular gas sufficient to cause the inner capillary tube to oscillate and generate a standing wave, as described earlier, is dependent upon the combination of the gas flow rate and the annular spacing between the inner and outer capillary tubes.

Figure 10:
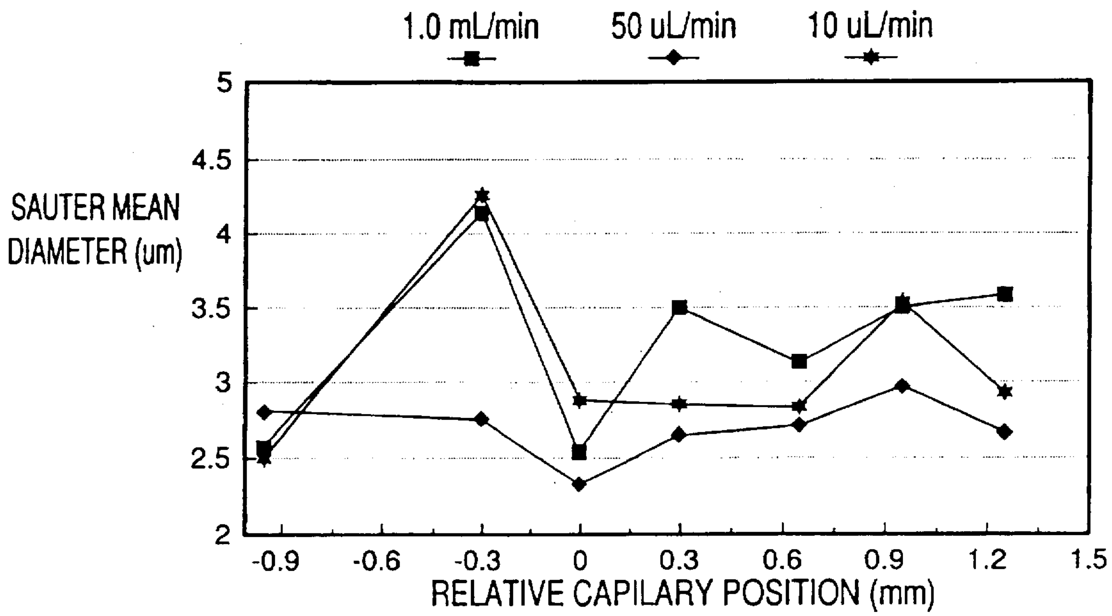
FIG. 10 illustrates the variation of Sauter mean droplet diameter with relative capillary position of the oscillating capillary nebulizer of the present invention.

FIG. 10 illustrates the results of our study of the relative axial positions of the inner and outer capillary tubes of our nebulizer at different liquid sample flow rates. In this study, the liquid capillary tube had an inner diameter of 50 μm and an outer diameter of 142 μm, while the gas capillary tube had an inner diameter of 250 μm and an outer diameter of 440 μm. 100% water was used as the liquid sample at a flow rate of 50 μl/min. Argon was used as the carrier gas at a flow rate of 0.90 l/min. The results show that our nebulizer generally performs best when the distal ends of the two capillaries are flush. At the lower micro flow rate of 10 μl/min our nebulizer performed best when the inner capillary tube is either flush with or extending slightly beyond the distal end of the outer gas capillary tube. In any event, the Sauter mean diameter of the primary aerosol observed with our nebulizer was typically less than 4.5 μm. This is in contrast to the mean diameters of 16–17 μm characterized by Shum et al. in their study of the Wiederan et al. direct injection nebulizer. See Shum et al. "Spatially Resolved Measurements of Size and Velocity Distributions of Aerosol Droplets From a Direct Injection Nebulizer", Appl. Spectrosc., 47, 575, 578 (1993).

Figure 11:
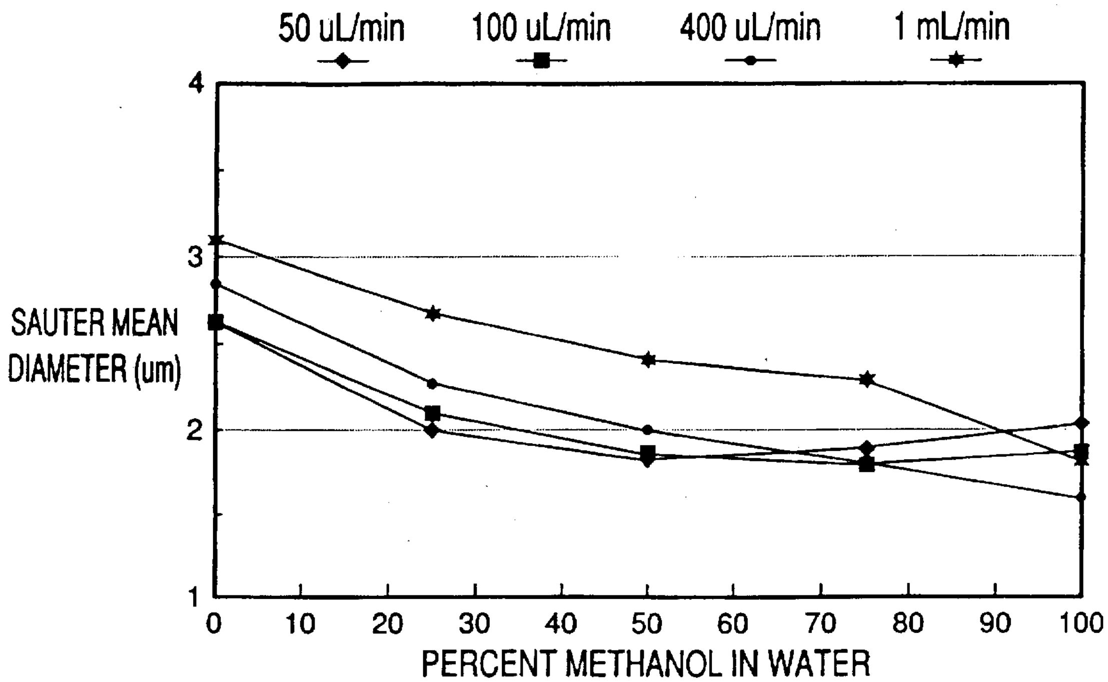
FIG. 11 illustrates the Sauter mean droplet diameter versus percent methanol and water at different liquid solvent flow rates for the oscillating capillary nebulizer of the present invention.

Our study of the effect on the Sauter mean diameter of the primary aerosol distribution achieved by our nebulizer as a function of percent methanol in water as the liquid sample stream at different liquid flow rates is reflected in FIG. 11. For this study, the nebulizer was constructed and operated in the same manner as for our study described above with respect to FIG. 10. The results show that the trend, as the percent of methanol in water increases, in the operation of our nebulizer is that only a small change in the mean particle size of the aerosol distribution is observed. Again, this is in stark contrast to the change observed by Shum et al. in their characterization of the Wiederin et al. direct injection nebulizer in which Shum et al. observed that the mean drop diameter of the direct injection nebulizer decreased by a factor of 2 or more as the amount of methanol was increased. See id., FIG. 2 at 577.

Figure 12:
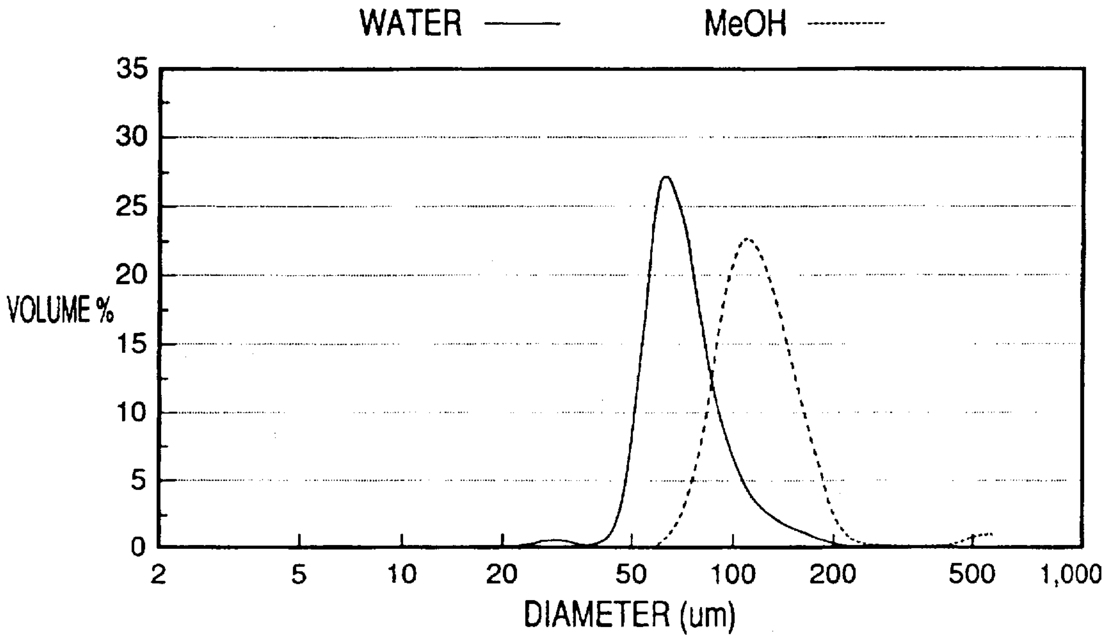
FIG. 12 illustrates spontaneous nebulizer particle size distributions of 100% methanol and 100% water.

FIG. 12 illustrates the results obtained when using as a spontaneous jet nebulizer for both 100% water and 100% methanol in the liquid flow streams. In this study, the nebulizer was operated providing a jet of liquid from the inner capillary and with no gas flow. In this operation, significantly larger particle size distributions were observed approximately two times or more the diameter of the liquid capillary tube. In addition, when operating with 100% methanol, the nebulizer gave larger droplets than when operating with 100% water. This is opposite to the results characterized by Shum et al. in their study of the direct injection nebulizer which showed that smaller droplets were obtained when operating with methanol. Id.

Figure 13A:
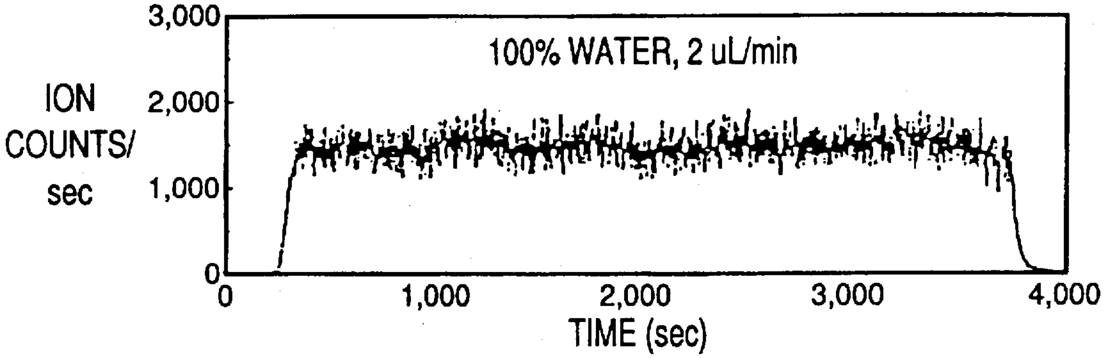
FIGS. 13*a* and *b* illustrate representative ICPMS traces for liquid solvents of 100% water and 100% methanol respectively over extended operation of the oscillating capillary nebulizer of the present invention.
Figure 13B:
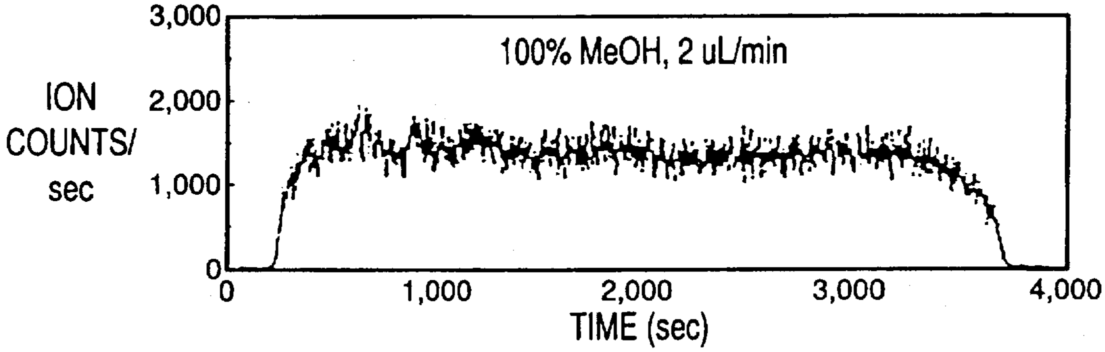
FIG. 13*c* illustrates a representative ICPMS trace for pulsed 1 μl aqueous liquid sample injections for the oscillating capillary nebulizer of the present invention.

FIG. 13*a* shows typical ICP/MS trace for our nebulizer for 100 ppb Rh (m/z=103) at a liquid flow rate of 2 μl/min in 100% water and a nebulizer gas flow of 1.10 l/min. FIG. 13*b* is an ICP/MS trace again for 100 ppb Rh (m/z=103). In this case, the liquid stream is 100% methanol at a flow rate of 2 μl/min., and the argon gas flow is 0.81 L/min. These traces represent approximately one hour continuous runs of our nebulizer operating at these conditions. The ICP/MS traces for 100% water and 100% methanol show that the our nebulizer is stable over extended runs.

Figure 13C:
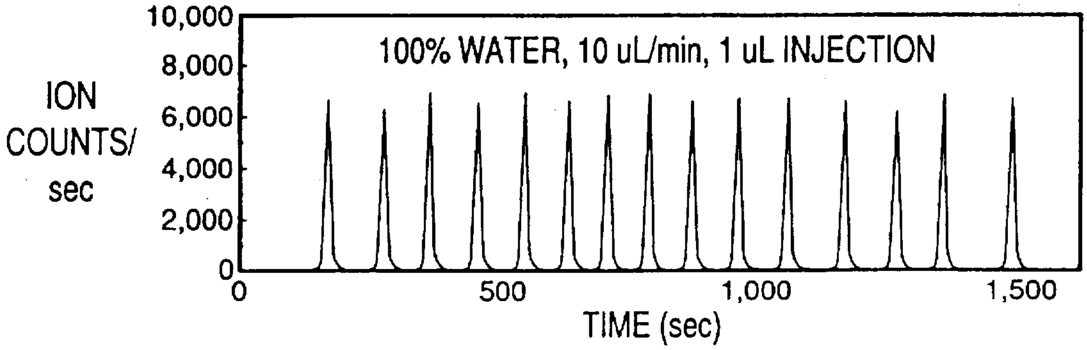

FIG. 13*c* is an ICP/MS trace for 100 ppb Rh (m/z=103) at a liquid flow rate of 10 μl/min for 100% water with 1 μl aqueous sample pulsed injections and an argon gas flow rate of 1.10 L/min. This trace shows the reproducibility of the results obtained by our nebulizer.

From the above discussion, it can be seen that our above described oscillating capillary nebulizer is capable of operating at micro flow liquid flow rates which are significantly lower than the flow rates at which known nebulizers may operate. Our nebulizer is also capable of producing a primary aerosol distribution having a mean droplet diameter which is smaller and more uniform than known nebulizers. Aerosol particle size and particle size distribution can be controlled by varying the dimensions of the inner and outer capillary tubes, by varying the location of the distal end of the inner capillary tube with respect to the location of the distal end of the outer capillary tube, and by varying the liquid and gas flow rates. Our nebulizer is operable over liquid flow rates of about 2 ml/min. and below. However, it performs better at micro flow rates of 50 μl/min and below and best at flow rates of below 30 μl/min. The preferable range for gas flow rates is approximately from 0.5 liters/min. to 1.0 liters/min. The preferred inner diameter of the inner capillary tube ranges from approximately 25 micrometers to approximately 103 micrometers. The preferred inner diameter of the outer capillary tube ranges from approximately 180 micrometers to 350 micrometers. The preferred annular spacing between the outer diameter of the inner capillary tube and the inner diameter of the outer capillary tube ranges from approximately 25 micrometers to approximately 75 micrometers. However, more important than the absolute values for these operating parameters is that the inner liquid capillary tube be made of a flexible material and that the annular spacing between the inner and outer capillary tubes in combination with the gas flow rate be such that the velocity of the gas flow imparts instability in the nebulizer causing the inner capillary tube to oscillate and generates a high frequency, ultrasonic standing wave along at least a portion of the liquid capillary tube.

Although the present invention has been described with reference to preferred embodiments, it will be apparent to those skilled in the art that variations and modifications of the present invention are within the spirit and scope of the present invention.

What is claimed is:

1. A nebulizer for nebulizing a liquid sample provided to said nebulizer, said nebulizer comprising:

a first outer capillary tube having an inner diameter and an outer diameter, a second flexible inner capillary tube having an inner diameter and an outer diameter, said outer diameter of said second flexible capillary tube being smaller than said inner diameter of said first capillary tube, said second capillary tube being coaxially arranged within said first capillary tube such that an annular spacing exists between the outer diameter of said second flexible capillary tube and the inner diameter of said first capillary tube, means for mounting said second flexible capillary tube and said first capillary tube in the coaxial arrangement, said second flexible capillary tube having a distal end and a proximal end, said means for mounting having a gas flow opening formed therein for allowing gas to flow into the space between the outer diameter of the flexible inner capillary tube and the inner diameter of the outer capillary tube, said proximal end of said second flexible inner capillary tube being open for allowing a liquid sample to be introduced into said second flexible capillary tube, and wherein gas is introduced through the gas flow opening and the liquid sample is introduced through the opening in said proximal end of said second flexible capillary tube at flow rates sufficient to cause liquid being projected from said distal end of said second flexible capillary tube to be nebulized due to oscillation of said second flexible capillary tube, wherein the gas flow rate generates a standing wave along the axial direction of at least a portion of said second flexible inner capillary tube which causes the liquid being projected from said distal end of said second flexible inner capillary tube to break up into substantially uniform droplets.

2. A nebulizer for nebulizing a liquid sample provided to said nebulizer according to claim 1 wherein said nebulizer further comprises means for effecting relative movement between said first outer flexible capillary tube and said second flexible inner capillary tube in the coaxial directions, wherein said means for effecting relative movement is connected to said first capillary tube at a location near the proximal end of said first capillary tube and to said second flexible capillary tube at a location near the proximal end of said second flexible capillary tube, said means for effecting relative movement substantially enclosing the proximal end of said first capillary tube to form a chamber within said first capillary tube, said second flexible capillary tube passing through said means for effecting relative movement to form the connection between said second flexible capillary tube and said means for effecting relative movement.

3. A nebulizer for nebulizing a liquid sample provided to said nebulizer according to claim 1 wherein said first and second capillary tubes are comprised of fused silica.

4. A nebulizer for nebulizing a liquid sample provided to said nebulizer according to claim 1 wherein said inner diameter of said second flexible capillary tube is sufficiently small to create a liquid stable flow at the liquid flow rate at which the liquid sample is introduced into said proximal end of said second flexible capillary tube.

5. A nebulizer for nebulizing a liquid sample provided to said nebulizer according to claim 1 wherein said nebulizer produces an aerosol at a liquid flow rate which is less than 30 microliters/min.

6. A nebulizer for nebulizing a liquid sample provided to said nebulizer according to claim 1 wherein the particle size and particle size distribution can be controlled by varying the dimensions of said first outer capillary tube and said second flexible inner capillary tube.

7. A nebulizer for nebulizing a liquid sample provided to said nebulizer according to claim 2 wherein the particle size and particle size distribution of the nebulized liquid can be varied by adjusting said means for effecting relative movement to thereby vary the distance between the distal end of said first outer capillary tube and the distal end of said second flexible inner capillary tube.

8. A nebulizer for nebulizing a liquid sample provided to said nebulizer according to claim 1 wherein the particle size and particle size distribution of the nebulized liquid can be varied by changing the liquid and sample gas flow rates.

* * * * *